United States Patent [19]

Drake

[11] Patent Number: 5,359,112
[45] Date of Patent: Oct. 25, 1994

[54] HYDROSILYLATION PROCESS

[75] Inventor: Robert A. Drake, Penarth, United Kingdom

[73] Assignee: Dow Corning Limited, Barry, Wales

[21] Appl. No.: 144,365

[22] Filed: Nov. 2, 1993

[30] Foreign Application Priority Data

Nov. 6, 1992 [GB] United Kingdom ............. 9223335

[51] Int. Cl.$^5$ .............................................. C07F 7/08
[52] U.S. Cl. ................................................ 556/479
[58] Field of Search .................................... 556/479

[56] References Cited

U.S. PATENT DOCUMENTS

| | | | |
|---|---|---|---|
| 2,823,218 | 2/1958 | Speier et al. | 556/479 |
| 3,188,299 | 6/1965 | Chalk | 260/46.5 |
| 3,631,086 | 12/1971 | Seyfried et al. | 556/479 |
| 3,925,434 | 12/1975 | Chuang | 556/479 |
| 4,292,434 | 9/1981 | Lindner | 556/479 |
| 4,398,010 | 8/1983 | Adkins | 556/479 X |
| 4,417,068 | 11/1983 | Kollmeier | 556/479 |
| 4,417,069 | 11/1983 | Brown | 556/479 |
| 4,578,496 | 3/1986 | Panster et al. | 556/479 |
| 4,584,361 | 4/1986 | Janik | 528/15 |
| 5,103,033 | 4/1992 | Bank | 556/479 X |
| 5,191,103 | 3/1993 | Mehta et al. | 556/479 |
| 5,258,480 | 11/1993 | Eckberg et al. | 556/479 X |
| 5,270,424 | 12/1993 | Drake et al. | 556/479 X |

FOREIGN PATENT DOCUMENTS 1454051 10/1976 United Kingdom .

*Primary Examiner*—Paul F. Shaver
*Attorney, Agent, or Firm*—Robert L. McKellar; William F. Boley

[57] ABSTRACT

Process for producing organosilicon compounds having silicon-bonded substituents, e.g. hexenyl, containing terminal olefinic unsaturation. Process comprises reacting ≡SiH with a diene in the presence of a mixture, and/or a reaction product, of a compound or complex of platinum and a compound having at least one amino group e.g. octylamine.

9 Claims, No Drawings

HYDROSILYLATION PROCESS

This invention relates to a process for the preparation of organosilicon materials and which involves the reaction of silicon compounds having ≡SiH groups with dienes.

The reaction of silicon compounds, for example silanes and polysiloxanes, having ≡SiH groups with compounds having olefinic or acetylenic unsaturation is well known. This procedure is often termed hydrosilylation or hydrosilation and is widely employed as a method of synthesis of organosilicon materials. A number of substances are known which are effective in catalysing the hydrosilylation reaction, the most common being the compounds and complexes of the transition metals such as platinum, rhodium and palladium. Specific examples of such catalysts are the platinum and rhodium halides, for example $H_2PtCl_6$, $PtCl_2$, $RhCl_3$, $RhCl_3(SEt_2)_3$ (where Et=ethyl), $Rh_2(CO)_4Cl_2$, complexes of platinum chlorides with siloxanes having unsaturated groups and complexes of platinum compounds with olefins.

A variety of organosilicon compounds can be synthesised by means of the hydrosilylation reaction. Organofunctional silanes and siloxanes may be obtained by the addition of ≡SiH in the silane or siloxane to an olefinically-unsaturated compound such as allyl chloride or allyl glycidyl ether. In a similar manner ≡SiH may be reacted with an olefin, for example hexene-1 or decene-1 to produce a silane or siloxane having respectively silicon-bonded hexyl or decyl groups. The hydrosilylation reaction may also be employed to react ≡SiH with dienes to obtain organosilicon compounds having silicon-bonded groups containing olefinic unsaturation. Such unsaturated organo-silicon compounds can be reacted with other SiH-containing organosilicon compounds to obtain useful products such as elastomers and coatings on plastic, paper and other substrates. However, we have found that during the hydro-silylation reaction some isomerisation of the diene occurs resulting in migration of the double bond from a terminal to an internal position in the desired silicon-bonded group. Products having such internal unsaturation exhibit low reactivity with respect to further hydrosilylation to produce elastomers and other products, and thus represent an undesirable component of the reaction product.

We have now surprisingly found that the amount of double bond migration that occurs during the addition of ≡SiH to dienes can be significantly reduced by the use of catalysts comprising a platinum compound or complex and a compound having therein at least one amino group.

G.B. Patent 1 054 658 discloses a process for producing a relatively stable organosilicon composition comprising an olefinic polysiloxane and a hydrogen-containing polysiloxane which comprises incorporating in the composition a mechanical mixture or a preformed complex of (i) a platinum-containing catalyst and (ii) a nitrogen-containing ligand selected from certain aliphatic and aromatic nitrogen compounds, or (iii) an organophosphorous ligand.

G.B. Patent 1 454 051 discloses ammonium-platinum-organosilicon compounds obtained by reacting chloroplatinic acid with an amino organosilicon compound. It also discloses the use of such compounds as hydrosilylation catalysts.

U.S. Pat. No. 4,292,434 teaches an improved process for the addition of silicon-bonded hydrogen to an aliphatic multiple bond, the improvement comprising carrying out the addition in the presence of a catalyst solution obtained from the reaction of a platinum halide with an olefin and thereafter heating the resultant solution with a primary or secondary amine.

In U.S. Pat. No. 4,417,068 there is disclosed a process for the addiiton of silanes or siloxanes having SiH groups to certain compounds with olefinic double bonds in the presence of a catalyst $YX_2(NH_3)_2$ in which Y is Pt or Pd and X is Cl, Br, I or $NO_2$.

U.S. Pat. No. 4,584,361 discloses a storage stable, heat-curable one part polyorganosiloxane composition consisting essentially of the product obtained by mixing (1) a vinyl-containing organosiloxane polymer, (2) an organohydrogen-siloxane, (3) a platinum catalyst and (4) a platinum catalyst inhibitor of the general formula $R^4NH_2$ or $R'_2NR^3NR^2_2$ in which R' is 1–4C alkyl, $R_2$ is R' or H, $R^3$ is alkylene of 2–4 carbon atoms and $R^4$ is 2–4C alkyl.

According to the present invention there is provided a process for the preparation of an organosilicon compound having at least one silicon-bonded hydrocarbon group containing terminal olefinic unsaturation which comprises reacting (A) a silicon compound having in the molecule at least one silicon-bonded hydrogen atom, with (B) a diene having from 6 to 14 carbon atoms and wherein the unsaturation is located at the terminal carbon atoms, in the presence of (C) a catalyst which comprises a mixture, and/or a reaction product, of a compound or complex of platinum and a compound having at least one amino group.

As the silicon compound (A) there may be employed in the process of this invention any monomeric, oligomeric or polymeric compound having at least one ≡SiH group. Such compounds and their use in hydrosilylation reactions are well documented in the art and include silanes, linear polysiloxanes, branched polysiloxanes and cyclic siloxanes. The nature of the silicon-bonded substituents present in addition to the hydrogen atoms is not critical but normally such substituents will be selected from monovalent hydrocarbon groups having from 1 to 10 carbon atoms and free of aliphatic unsaturation, halogen atoms and alkoxy groups having less than about 8 carbon atoms. Specific examples of silicon-bonded substituents are, therefore, methyl, ethyl, n-propyl, butyl, octadecyl, chlorine, methoxy, ethoxy, isopropoxy and butoxy. Examples of compounds (A) are $C_6H_5SiHCl_2$, $HSi(OCH_3)_3$, $HSiCl_3$, $CH_3HSi(OC_2H_5)_2$, $(CH_3)_2HSiCl$, methylhydrogen polysiloxanes and copolymers of methylhydrogensiloxane units with one or more other siloxane units, for example dimethylsiloxane, trimethyl-siloxane and dimethylhydrogensiloxane units. The process of the invention is, however, of particular interest in connection with the reactions of chlorosilanes, for example $CH_3HSiCl_2$ and $HSiCl_3$ which appear to show the greatest reduction in internal bond migration in the product.

Reactant (B) may be any diene having from 6 to 14 carbon atoms and in which the olefinic unsaturation is non-conjugated and is present at the terminal carbon atoms, for example 1,5-hexadiene, 1,9-decadiene, 1,11-dodecadiene and 1,13-tetradecadiene. In general the preferred dienes are those having from 6 to 10 carbon atoms.

The catalyst (C) comprises a mixture, and/or a reaction product, of a platinum compound or complex and a compound having at least one amino group. Any compound or complex of platinum which is effective as a hydrosilylation catalyst may be employed. A wide variety of such compounds and complexes are known and include, for example, chloroplatinic acid, platinous chloride, platinic bromide, salts of chloroplatinous acids e.g. $Na_2PtCl_4$, platinum acetyl-acetonate, complexes of platinum halides with alcohols and aldehydes and complexes of platinum halides with organic and organosilicon compounds having olefinic unsaturation such as cyclopentene, cyclohexene, cyclopropane and 1,3-divinyltetramethyldisiloxane- The preferred platinum component of the catalyst (C) are the platinum halides and salts thereof, chloroplatinic acid and complexes of platinum halides e.g. platinic chloride and chloroplatinic acid with siloxane oligomers having silicon-bonded vinyl groups, the latter complexes being most preferred.

As the compound having amino groups there may be employed organic (including aliphatic and aromatic) amines and polyamines, and organosilicon compounds having silicon-bonded groups containing at least one amino group. The amino groups may be primary, secondary or tertiary. Examples of operative amines are n-butylamine, n-octylamine, decylamine, cyclohexylamine, triethylamine, ethylenediamine, tetramethylenediamine, diethylene triamine, tetramethylethylenediamine, $C_6H_{11}NH(CH_2)_3SiCH_3(OC_2H_5)_2$, $NH_2(CH_2)_4Si(OCH_3)_3$, $H_2N(CH_2)_2NHCH_2CH(CH_3)CH_2Si(OC_2H_5)_3$, $H_2N(CH_2)_2NH(CH_2)_2NH(CH_2)_3Si(OC_4H_9)_3$, $[H_2N(CH_2)_3Si(CH_3)_2]_2O$ and $CH_3Si(NHC_4H_9)_3$. Also exemplary of the operative amino compounds are those wherein the nitrogen atom or atoms are present in aliphatic or aromatic hetero-cyclic compounds, for example pyridine, and those wherein the amine group is attached to an aromatic ring either directly or by way of an aliphatic carbon bridge, for example aniline and benzylamine. In general the preferred compounds containing amino groups are the aliphatic amines and polyamines.

The relative proportions of amine to platinum compound or complex may vary between wide limits. Proportions which provide as little as 0.5 atom of nitrogen in the amine per atom of platinum can produce a reduction in the amount of the undesired isomer in the product. If desired the amine may be employed in a proportion which provides up to 50 atoms or more of amine nitrogen per atom of Pt. However, in most cases no advantage accrues from the use of such high proportions and in general it is preferred that the amine compound provides from 1 to 15 atoms of nitrogen per atom of platinum.

Reaction between the silicon-hydrogen compound (A) and the diene (B) may be carried out employing any conventional process techniques. For example it may be performed at atmospheric, sub-atmospheric or super-atmospheric pressures, in the presence or absence of solvents and at temperatures from below 20° C. to above 160° C. Normally it is preferred to expedite the reaction by employing temperatures in the range from about 60° C. to about 180° C. and, if desired, super-atmospheric pressure. In order to minimise the reaction of the silicon-hydrogen compound with both of the unsaturated groups in the diene, the diene is preferably employed in an excess of at least twice the stoichiometric amount. The mixture of the amino compound and platinum compound or complex which comprise catalyst (C) may be formed in situ by incorporating these two components separately in the reaction mixture. However, some experiments have indicated improved results if the amine and platinum compound or complex are mixed together prior to incorporation with (A) and (B).

The products obtained by the process of this invention are silanes and siloxanes which have therein at least one silicon-bonded hydrocarbon group containing olefinic unsaturation. By employing the catalyst (C) it has been found possible to obtain a product wherein the proportion of non-terminal olefinic unsaturation is significantly reduced compared with processes employing more conventional platinum-containing catalysts. The products of the process of this invention may be employed in the preparation of organosilicon compositions, for example elastomers and coating compositions where they may be cured by hydrosilylation or other reactions.

The following Examples in which Me represents methyl and Et represents ethyl illustrate the invention.

EXAMPLE 1

A series of experiments to react 1,5-hexadiene with $HMeSiCl_2$ was performed according to the following general procedure.

To a 250ml flask fitted with a condenser, dropping funnel, mechanical stirrer and temperature probe were added 1,5-hexadiene (49.2g, 0.6 mol), platinum catalyst ($10^{-5}$ mol Pt) and the required amount of octylamine. The dropping funnel was charged with $HMeSiCl_2$ (23g, 0.2 mol). The contents of the flask were heated to reflux (59° C.) and the dropwise addition of $HMeSiCl_2$ commenced. On completion of the addition of the $HMeSiCl_2$ the reflux temperature rose to 72° C. indicating that the reaction was complete. The time required to this point was approximately one hour.

The reaction mixture was allowed to cool and the excess hexadiene removed under reduced pressure to leave hexenylmethyldichlorosilane. Analysis by gas chromatography was then employed to determine the percentage of product in which isomerisation resulting from migration of the double bond had occurred. The results obtained employing four different platinum catalysts are set out in the following table.

| Ratio | % isomerisation | | | |
|---|---|---|---|---|
| N:Pt | $H_2PtCl_6.6H_2O$ (a) | $Na_2PtCl_4$ | Pt (b) | Pt (c) |
| 0:1 | 33 | 34 | 30 | 21.4 |
| 2:1 | 5.4 | 3.4 | 4.8 | 3.0 |

(a) in isopropyl alcohol
(b) complex of $H_2PtCl_6.6H_2O$ and divinyltetramethyldisiloxane
(c) complex of $PtCl_2$ and divinyltetramethyldisiloxane.

EXAMPLE 2

The procedure of Example 1 was repeated employing Pt(c) as the platinum compound and with differing octylamine proportions to provide various ratios of N to Pt atoms. Measurement of the percentage isomerisation for each ratio gave the values shown in the following table.

| Ratio N:Pt | 0:1 | 0.5:1 | 2:1 | 2:1 (d) | 50:1 |
|---|---|---|---|---|---|
| isomerisation | 21.4 | 17.7 | 3.0 | 1.0 | <1.0 |

(d) platinum complex and octylamine premixed 16 hour prior to use.

EXAMPLE 3

The general procedure described in Example 1 was repeated except that the octylamine was replaced in turn with other amines. The Pt compound used in the reaction was Pt(c). As indicated in the table below each of the amines was effective in significantly reducing the percentage isomerisation.

| Amine | N:Pt | % isomerisation |
|---|---|---|
| Et$_3$N | 2:1 | <1.0 |
|  | 50:1 | <1.0 |
| TMEDA | 2:1 | <1.0 |
|  | 50:1 | 4.1 |
| Amine A | 2:1 | 4.9 |
| Amine B | 50:1 | <1.0 |
| Pyridine | 2:1 | 7.7 |
|  | 50:1* | <1.0 |

TMEDA = tetramethylethylenediamine
Amine A = (MeO)$_3$Si(CH$_2$)$_3$NH$_2$
Amine B = (MeO)$_3$Si(CH$_2$)$_3$NHCH$_2$CH$_2$NHCH$_2$CH$_2$NH$_2$
*slow reaction

EXAMPLE 4

The general procedure of Example 1 was employed to react 1,5-hexadiene with respectively (x) HMe$_2$SiCl, (y) HSiCl$_3$ and (z) Me$_3$SiO(SiHMeO)$_2$SiMe$_3$ employing Pt(c) as the catalyst in the presence of a molar ratio of octylamine to Pt of 2:1. Measurement of the percentage isomerisation gave the following results.

| Reactant | % isomerisation |
|---|---|
| x | 4.8 |
| y | 1.9 |
| z | 0.9 |

EXAMPLE 5

The procedure of Example 1 was employed to react 1,9-decadiene with HMeSiCl$_2$ employing Pt(c) in the presence of a molar ratio of octylamine to Pt of 2:1. The product decenylmethyldichlorosilane had a content of the isomerised material of 15% by weight. When the reaction was repeated with the octylamine omitted the content of isomerised product was 33% by weight.

That which is claimed is:

1. A process for the preparation of an organosilicon compound having at least one silicon-bonded hydrocarbon group containing terminal olefinic unsaturation which comprises reacting (A) a silicon compound having in the molecule at least one silicon-bonded hydrogen atom, with (B) a diene having from 6 to 14 carbon atoms and wherein the unsaturation is located at the terminal carbon atoms, in the presence of (C) a catalyst selected from mixtures and reaction products of a compound of platinum and a compound having at least one amino group.

2. A process as claimed in claim 1 wherein the compound having at least one amino group is selected from aliphatic amines and aliphatic polyamines.

3. A process as claimed in claim 1 wherein the silicon compound (A) is a chlorosilane.

4. A process as claimed in claim 1 wherein the compound having at least one amino group and the platinum compound are mixed together prior to incorporation with (A) and (B).

5. A process for the preparation of an organosilicon compound having at least one silicon-bonded hydrocarbon group containing terminal olefinic unsaturation which comprises reacting (A) a silicon compound having in the molecule at least one silicon-bonded hydrogen atom, with (B) a diene having from 6 to 14 carbon atoms and wherein the unsaturation is located at the terminal carbon atoms, in the presence of (C) a catalyst selected from mixtures and reaction products of a complex of platinum and a compound having at least one amino group.

6. A process as claimed in claim 5 wherein the compound having at least one amino group is selected from aliphatic amines or polyamines.

7. A process as claimed in claim 5 wherein the silicon compound (A) is a chlorosilane.

8. A process as claimed in claim 5 wherein the platinum-containing complex is a complex formed between a platinum halide and a siloxane oligomer having silicon-bonded vinyl groups.

9. A process as claimed in claim 5 wherein the compound having at least one amino group and the platinum complex are mixed together prior to incorporation with (A) and (B).

* * * * *